US006594522B1

(12) United States Patent
Korenaga

(10) Patent No.: US 6,594,522 B1
(45) Date of Patent: Jul. 15, 2003

(54) THERAPEUTIC DEVICE FOR GENERATING LOW-OR MIDDLE-FREQUENCY ELECTROMAGNETIC WAVES

(75) Inventor: Tetsuya Korenaga, 8-17 Heiwa 3-chome, Chuo-ku, Fukuoka-shi, Fukuoka 810-0016 (JP)

(73) Assignee: Tetsuya Korenaga, Fukuoka (JP)

( * ) Notice: Subject to any disclaimer, the term of this patent is extended or adjusted under 35 U.S.C. 154(b) by 0 days.

(21) Appl. No.: 09/674,012

(22) PCT Filed: Feb. 25, 1999

(86) PCT No.: PCT/JP99/00911

§ 371 (c)(1),
(2), (4) Date: Oct. 24, 2000

(87) PCT Pub. No.: WO00/50118

PCT Pub. Date: Aug. 31, 2000

(51) Int. Cl.[7] .................................. A61N 1/32
(52) U.S. Cl. ........................ 607/2; 607/153; 607/149
(58) Field of Search ................. 607/153, 3, 1, 607/2, 80, 115, 149, 104; 600/387; 606/33, 32, 41

(56) References Cited

U.S. PATENT DOCUMENTS

| 3,640,270 A | * | 2/1972 | Hoffmann | ................... 600/387 |
|---|---|---|---|---|
| 4,169,293 A | * | 10/1979 | Weaver | ........................ 4/541.2 |
| 5,423,811 A | * | 6/1995 | Imran et al. | .................... 606/41 |
| 5,688,267 A | * | 11/1997 | Panescu et al. | ................ 606/31 |
| 5,951,546 A | * | 9/1999 | Lorentzen | ..................... 606/41 |
| 6,032,077 A | * | 2/2000 | Pomeranz | ..................... 606/32 |
| 6,053,912 A | * | 4/2000 | Panescu et al. | ................ 606/40 |

FOREIGN PATENT DOCUMENTS

| DE | 3228143 A1 | * | 2/1984 | ............ A61N/1/04 |
|---|---|---|---|---|
| JP | 04197269 A | * | 7/1992 | ............ A61N/1/06 |
| JP | 5-293182 A | | 5/1993 | |
| JP | 11-57029 A | | 11/1999 | |
| WO | WO 91/15996 | * | 10/1991 | ......... A61B/5/0408 |

OTHER PUBLICATIONS

Japanese Utility Model Publication No. 30788/1926 (Shouichirou Tanaka) Nov. 8, 1926 (and English translation).

* cited by examiner

*Primary Examiner*—Kennedy Schaetzle
(74) *Attorney, Agent, or Firm*—Shanks & Herbert

(57) ABSTRACT

An electric therapeutic device having easy operability and improved therapy effects for treating the affected part of a user with electric current flowing from a conductor (3) attached to the affected part, including a hot water or cold water circulator (4) for circulating hot or cold water in the conductor (3).

18 Claims, 8 Drawing Sheets

THERAPEUTIC DEVICE FOR GENERATING LOW-OR MIDDLE-FREQUENCY ELECTROMAGNETIC WAVES

TECHNICAL FIELD

The present invention relates to an electric therapeutic device.

BACKGROUND TECHNOLOGY

A conventional electric therapeutic device is usually composed of an oscillator for generating electromagnetic waves and a conductor connected to the oscillator. The conductor has an opening formed at the bottom portion of a flexible case and an electrode at the top portion thereof. An electrode pad having a water-absorbing property is disposed in the position immediately below the electrode. The conductor is connected to a suction pump.

Upon conducting therapy using such a conventional electric therapeutic device, the conductor is attached to an affected part of a user in the state in which the electrode pad is absorbed with water, and it is allowed to be closely attached to the affected part of the user by sucking air in the case by operating the suction pump.

It has been found, however, that such a conventional electric therapeutic device has the disadvantage that the conductor is caused to be detached or removed from the affected part of the user because the conventional electric therapeutic device sucks water absorbed in the electrode pad, too, together with the air present in the case, on account of the fact that the conductor is closely attached to the affected part of the user and that, upon continually operating the electric therapeutic device, a large amount of the water is sucked from the electrode pad and the electrode pad becomes too dry so that the electric property is worsened and the ability of attachment of the conductor to the affected part is decreased.

DISCLOSURE OF THE INVENTION

The electric therapeutic device according to the present invention is composed of, an oscillator, a conductor connected to the oscillator, and a water circulator for circulating hot or cold water to the conductor.

The water circulator has a water reservoir container connected to the conductor through a water supply pipe and the conductor is connected to a suction pump through a water return pipe. The suction pump is then connected to the water reservoir through a communicating pipe.

The conductor is provided with an electrode at the top portion of the case having an opening at the bottom portion thereof and with the electrode pad immediately under the electrode.

The electrode is provided with a water supply passage and a water return passage, and the water supply pipe is coupled with the water supply passage while the water return pipe is coupled with the water return passage.

The electrode pad or the case is formed with a circulator for circulating hot water.

The electric therapeutic device according to the present invention is adapted to conduct treatment of an affected part of a user by means of the action of electricity flowing through the affected part thereof by closely attaching the opening of the conductor to the affected part and discharging electricity toward the affected part from the electrode of the conductor.

By circulating hot water by the hot water circulator upon treatment, the electrode pad is brought into a state in which it contains water so that it can improve electric properties of the electrode by the action of water due to the fact that water is always present between the electrode and the affected part of a user.

Moreover, the temperature on the affected part of the user becomes appropriate by holding the circulating water at an appropriate temperature so that comfort to use by the user can be improved and the hot-temperature effect can be provided by the action of hot water. Further, the electric therapeutic device can improve the therapy effects.

In addition, the air present in the case of the conductor is sucked out by the suction pump so that the conductor can be attached to the affected part of a user with ease simply by placing the conductor on the affected part thereof and that the attachment property of the conductor to the affected part thereof can be improved.

BRIEF DESCRIPTION OF THE ACCOMPANYING DRAWINGS

BEST MODE FOR CARRYING OUT THE INVENTION

The present invention will be described in more detail by way of examples with reference to the accompanying drawings.

Figure 1:
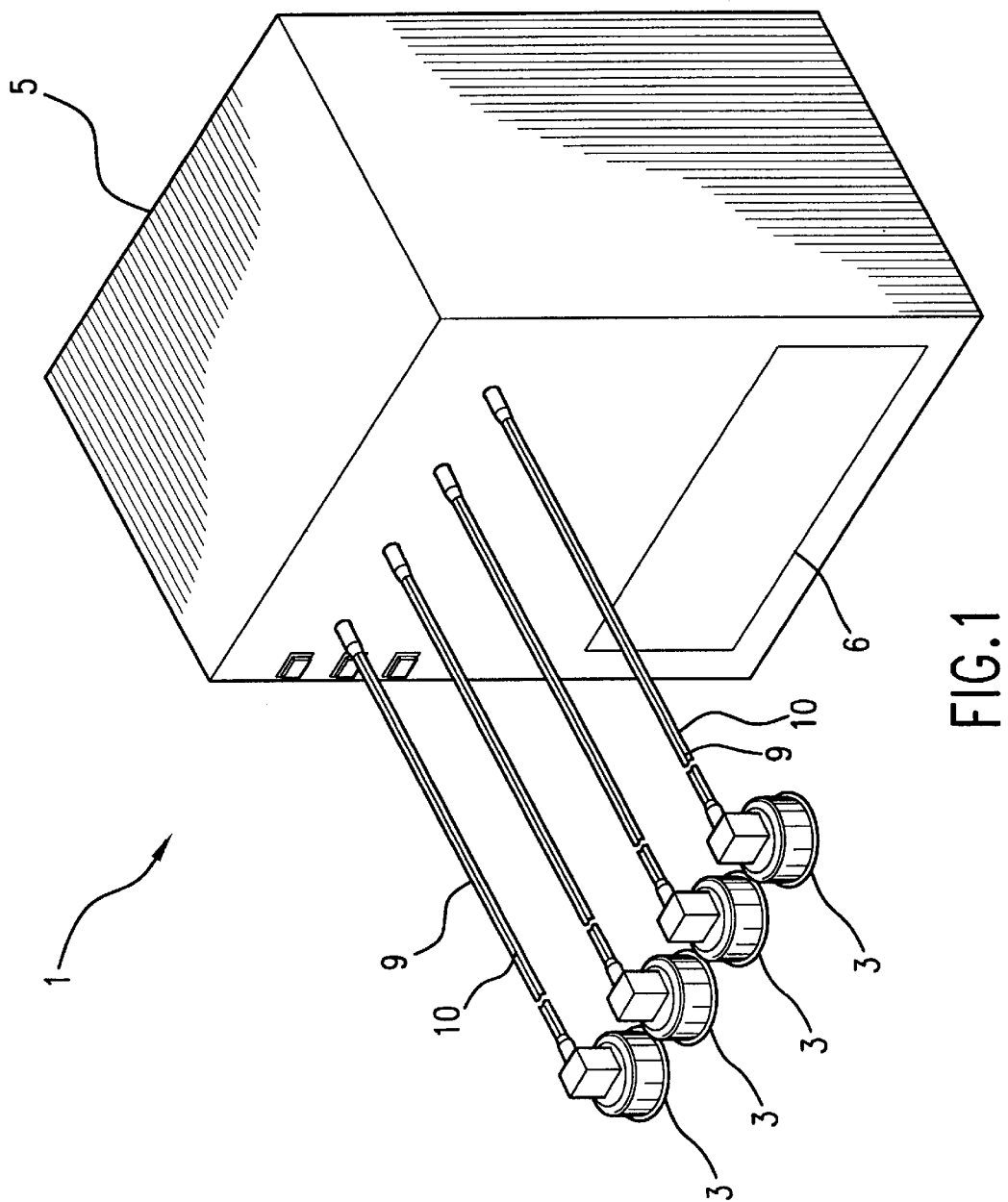
FIG. 1 is a perspective view showing an electric therapeutic device according to the present invention.
Figure 2:
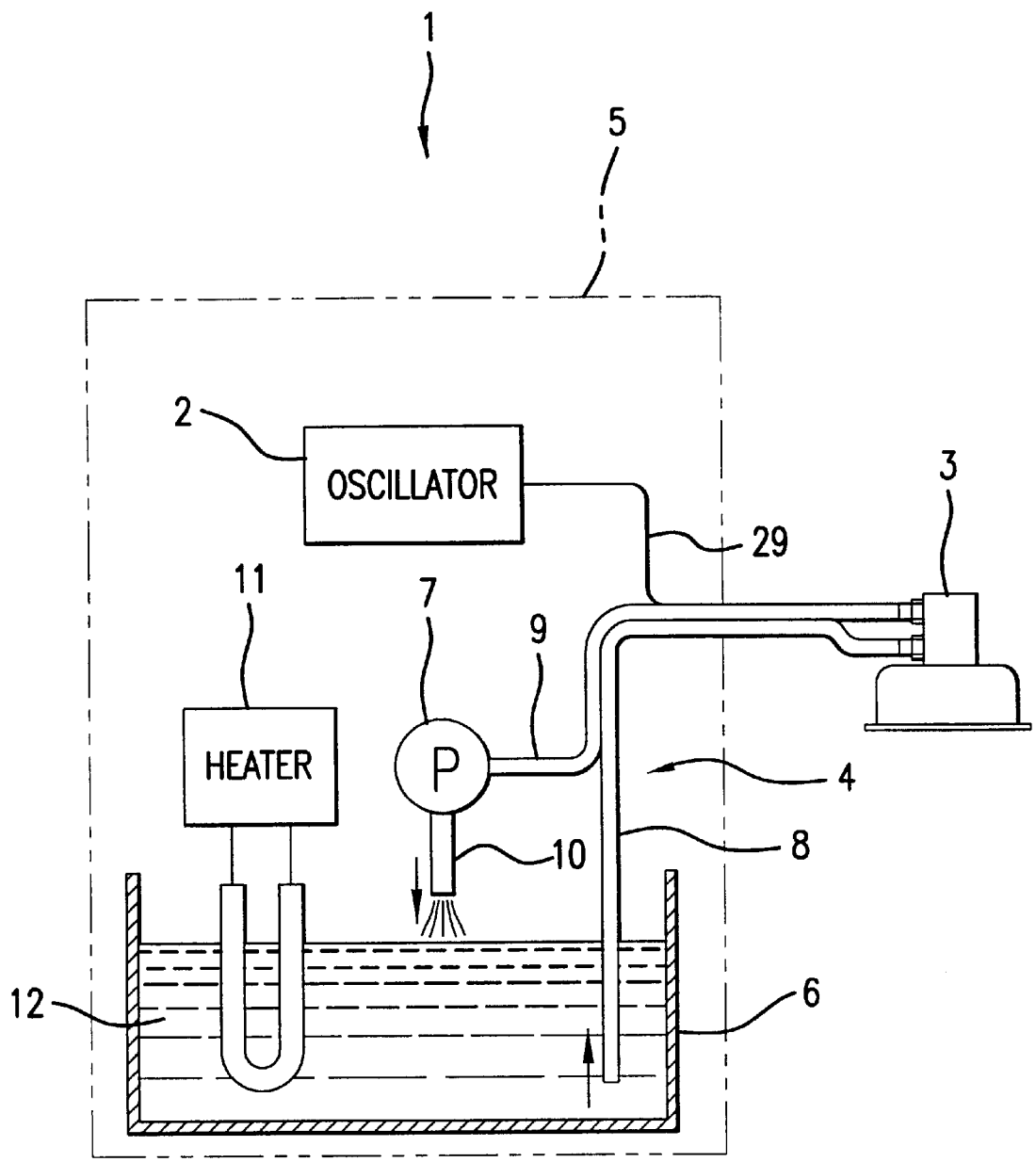
FIG. 2 is a schematic illustration showing the electric therapeutic device of FIG. 1.

FIGS. 1 and 2 show each an electric therapeutic device 1 according to the present invention. The electric therapeutic device 1 comprises an oscillator 2 for generating electromagnetic waves; a conductor 3 connected to the oscillator 2, and a water circulator 4 for circulating hot or cold water to the conductor 3.

The oscillator 2 is an apparatus for generating electricity for use in treating the affected part of a user and is disposed at the upper portion of a case 5 for the main body of the device, the case being in the form of a rectangular box. Although electricity for use in treating the affected part thereof may be the one of a low-frequency wave having frequency mainly in the range of from 3 to 1,000 Hz, there may be used a medium frequency wave of an interference type having a frequency range of from 4,000 to 5,000 Hz or direct current in accordance with treatment purposes.

The hot-water or cold-water circulator 4 has a water reservoir container 6 disposed at the lower portion of the case 5 and a suction pump 7 disposed above the heater reservoir 6. The water reservoir 6 is connected to the conductor 3 through a water supply pipe 8, and the conductor 3 is connected to the suction pump 7 through a water return pipe 9 that is in return communicated with and connected to the water reservoir 6 through a communicating, pipe 10.

The water reservoir 6 is provided with a heater 11 in order to maintain the temperature of the water 12 inside the water reservoir 6 at an appropriate level, e.g., at about 40° C.

Figure 3:
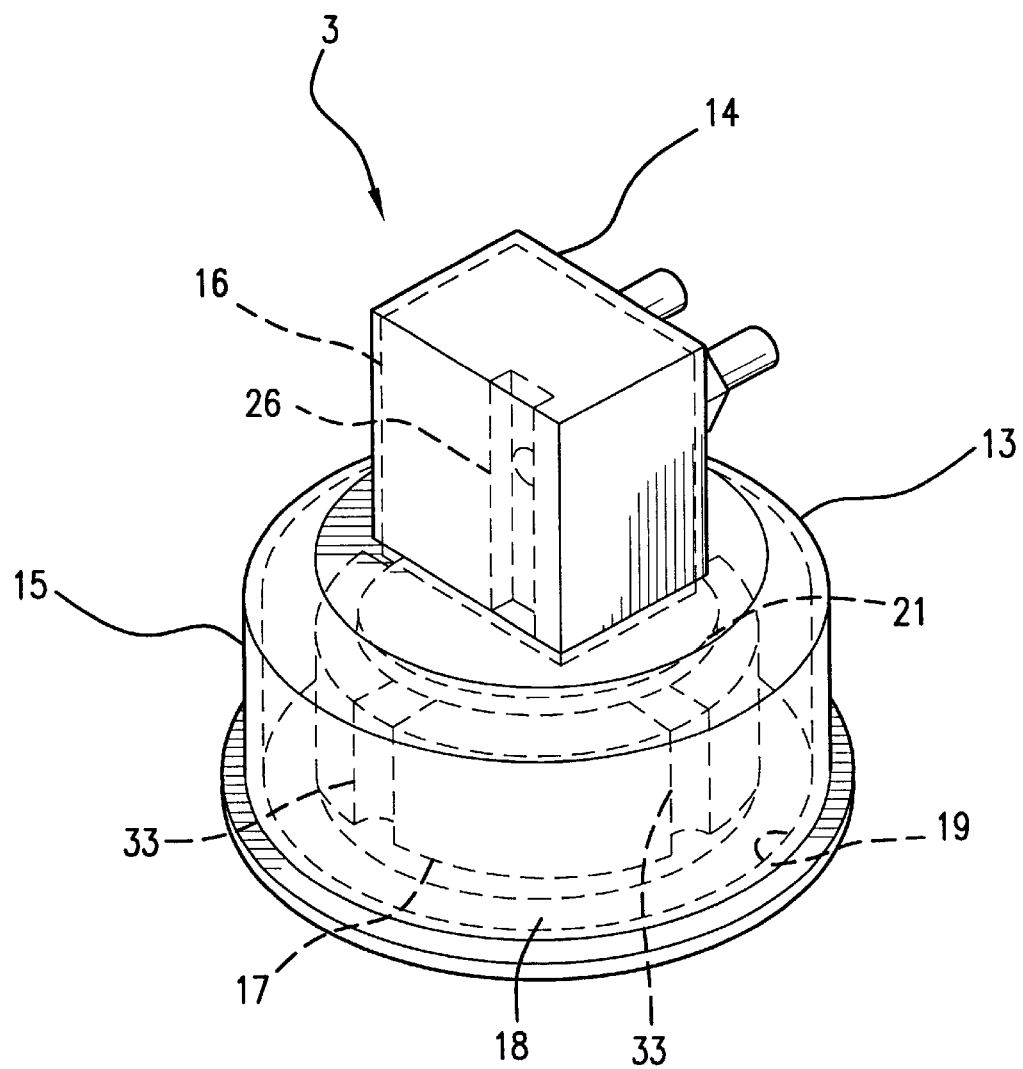
FIG. 3 is a perspective view showing a conductor.
Figure 4:
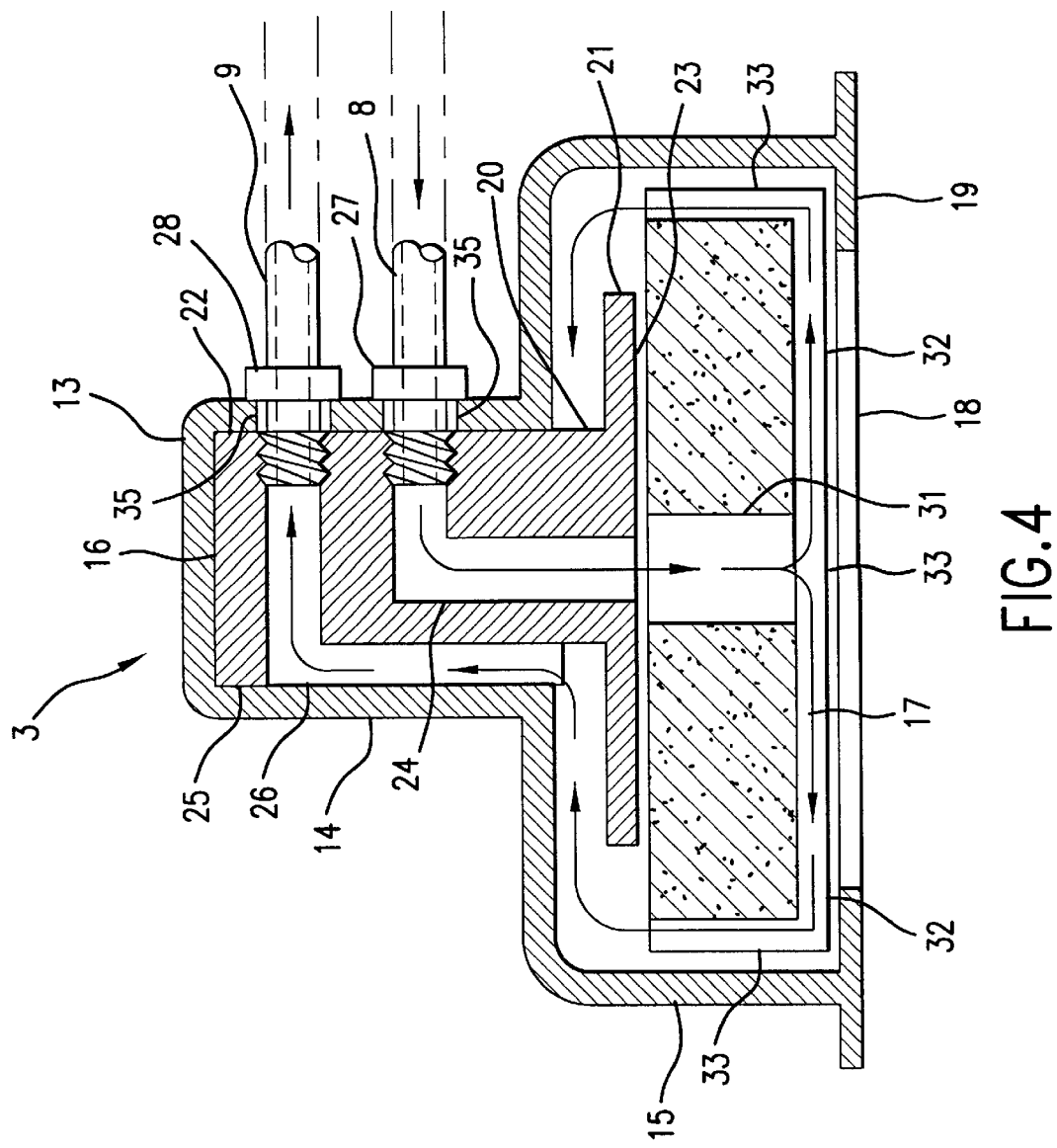
FIG. 4 is a sectional illustration showing the circulation of hot water in the conductor.

As shown in FIGS. 3 and 4, the conductor 3 has an electrode accommodation section 14 of a rectangular form on a flexible case 13, the electrode accommodation section being adapted to accommodate an electrode. Moreover, it has an electrode pad accommodation section 15 in a cylindrical form on the bottom portion of the electrode accommodation section 14 that accommodates an electrode 16. On the other hand, the electrode pad accommodation section 15 accommodates an electrode pad 17.

The conductor 3 is provided with a circular aperture 18 at the bottom of the electrode pad accommodation section 15 of the case 13. Moreover, a guard member 19 is disposed on the inner edge portion of the circular aperture 18 and holds the electrode pad 17 so as to prevent the electrode pad 17 from falling out of the aperture 18.

As shown in FIGS. 3 and 4, the electrode 16 forms an electrode plate 21 in the form of a disk on the bottom portion of the main body of the electrode in the form of a rectangular box. The bottom face of the electrode plate 21 is disposed to constitute an electrode face 23 so as to generate electricity toward the affected part of a user.

The electrode 16 forms a communicating passage 24 on the supply path side extending from the right-hand side portion of a front face 22 of the electrode main body 20 toward the central portion of the electrode face 23 of the electrode plate 21. On the other hand, it forms a communicating passage 26 on the return path side extending from a rear face 25 of the electrode main body 20 toward the left-hand side portion of the front face 22 of the electrode main body 20. The communicating passage 24 is connected to the supply pipe through a nipple 27, and the communicating passage 26 is connected to the return pipe 9 with a nipple 28. The nipples 27 and 28 are in turn inserted through holes 35 and 36, respectively, each being inserted in an apart spaced relationship over the entire length through the case 13 and screwed therein with temp 20. The nipples 27 and 28 hold the electrode 16 on the case 13.

As the electrode 16 is provided with the communicating passage 24 on the supply path side and the communicating passage 26 on the return path side, hot water 12 can be smoothly circulated through the case 13.

Each of the supply pipe 8 and the return pipe 9 may be made of a flexible polyvinyl material. The outer peripheral surface of the return pipe 9 may be covered with a metal wire 29 that in turn is electrically insulated on its outer peripheral surface while that electrically couples the electrode 16 with the oscillator 2, as shown in FIG. 2. The metal wire 29 may be disposed on the supply pipe 8 in place of the return pipe 9 or on both the return pipe 9 and the supply pipe 8.

The integral construction of the metallic wire 29 for connecting the electrode 16 with the oscillator 2 and the pipes 8 and 9 for circulating hot water 12 can reduce the wiring between the oscillator 2 and the conductor 3.

Figure 5:
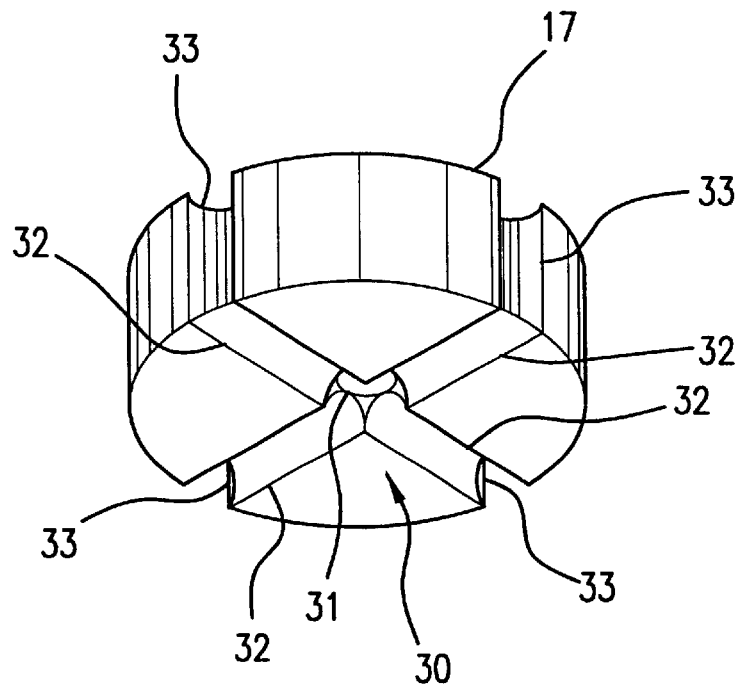
FIG. 5 is a perspective view showing an electrode pad.

As shown in FIGS. 3 to 5, the electrode pad 17 may be made of a water-absorptive sponge in the form of a column and forms a circulating passage 30 for circulating hot water 12. More specifically, the electrode pad 17 is provided with a communicating aperture 31 at its central portion, which extends over its entire thickness so as to communicate with the supply passage 24 of the electrode 16. Further, it is provided with four bottom passages 32 in its bottom surface, each bottom passage extending in a radial direction from the communicating aperture 31. Moreover, a communicating side passage 33 is formed along and in the side of the electrode pad 17, which continually extends from the edge of the corresponding bottom passage 33 so as to communicate with the return passage 26 of the electrode 16. With the arrangement as described above, the communicating aperture 31 as well as the bottom passages 31 and the communicating side passages 33 constitute the circulating passage 30.

Figure 6:
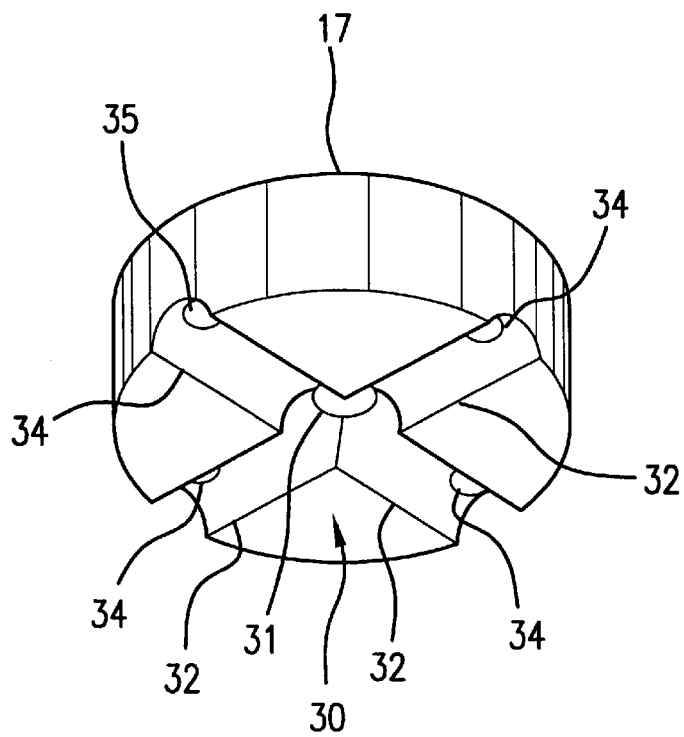
FIG. 6 is a perspective view showing another embodiment of an electrode pad.

FIG. 6 shows another embodiment of the electrode pad 17. This electrode pad 17 is provided with a communicating side aperture 34 at an edge portion of each of the bottom passages 32, which extends over its entire thickness. With the arrangement of the passages as shown in FIG. 6, the communicating aperture 31 and the communicating side apertures 34 as well as the bottom passages 32 constitute the circulating passage 30.

Figure 7:
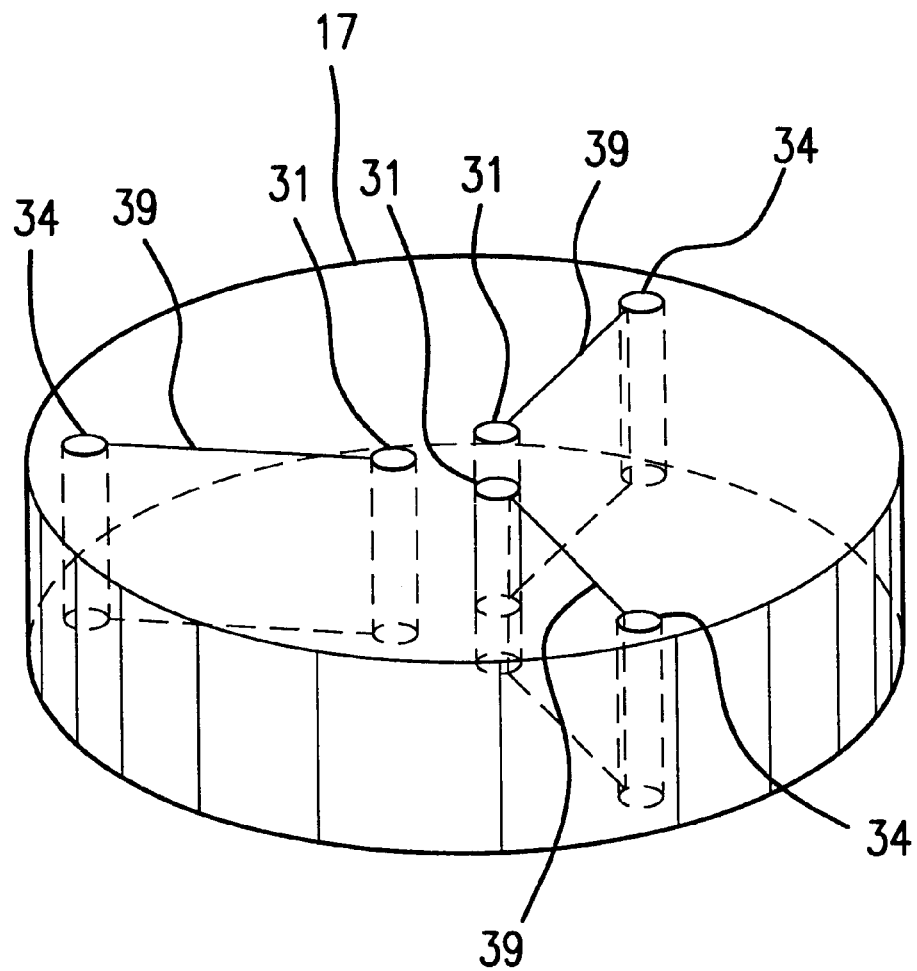
FIG. 7 is a perspective view showing a further embodiment of an electrode pad.

Likewise, FIG. 7 shows another embodiment of the electrode pad 17. The electrode pad 17 is provided with three communicating apertures 31 at a central portion thereof, each communicating aperture extending over its entire thickness so as to communicate the top face with the bottom face thereof. At the outer edge portion of the electrode pad 17 are provided three communicating side apertures 34 each of which is located in a radial direction from the communicating central apertures 31. A communicating slit-shaped aperture 39 is provided each between the communicating central apertures 31 and the corresponding side apertures 34 so as to communicate the peripheral wall edge of the central aperture 31 with the peripheral wall edge of the side aperture 34. The slit-shaped apertures 39 can action circulating the hot water 12 throughout the inside of the electrode pad 17.

The formation of the electrode pads 17 in the configurations as described above allows a smooth circulation of hot water 12 throughout the electrode pad 17.

Figure 8:
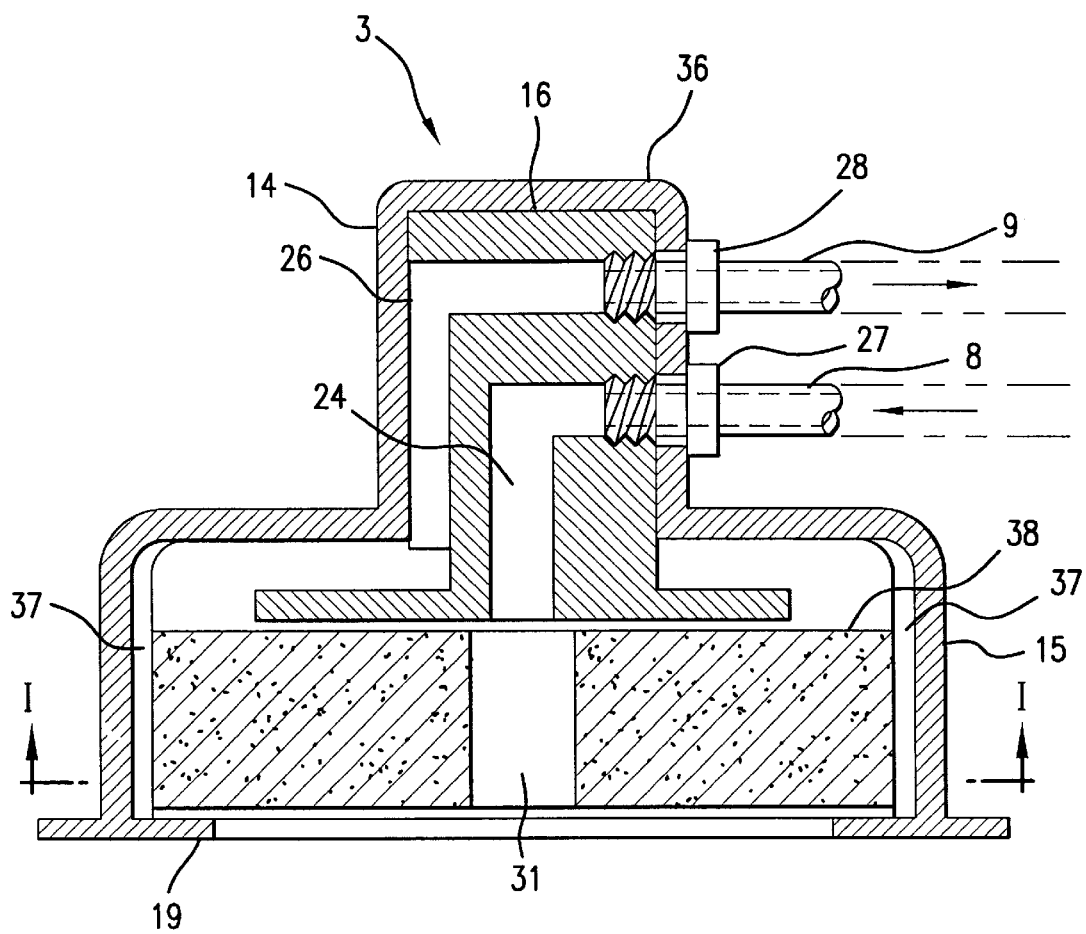
FIG. 8 is a perspective view showing a further embodiment of an electrode pad and a case.
Figure 9:
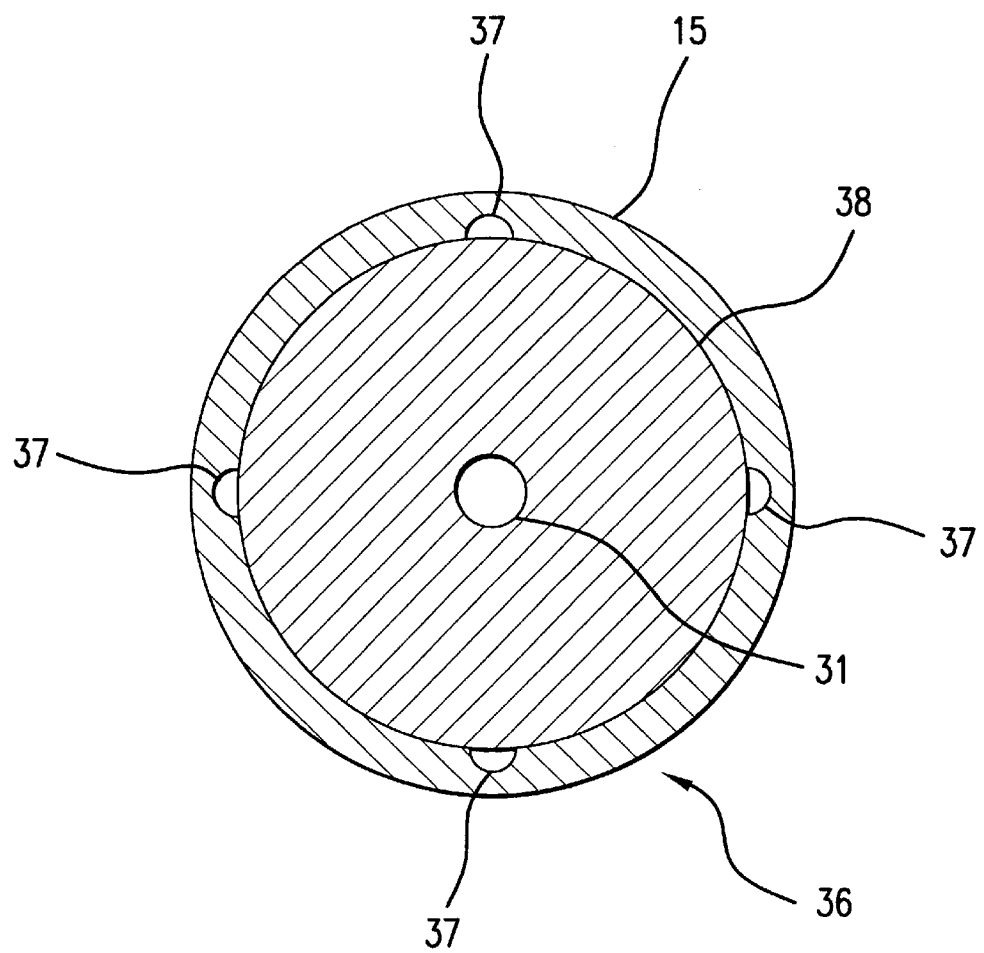
FIG. 9 is a section view when taken along line I—I of FIG. 8.

FIGS. 8 and 9 shows another embodiment of the conductor 3 according to the present invention. In this embodiment, there is used an electrode pad 33 in the form of a column, which is provided with a communicating central aperture 31 at its central portion communicating with the supply passage 24 of the electrode 16. Furthermore, a communicating side groove 37 communicating the top face with the bottom face is formed in the inner peripheral wall side of the electrode pad accommodation section 15 of the case 36 so as to circulate hot water 12 throughout the electrode pad.

The formation of the communicating side grooves 37 inside the case 36 can also serve as circulating the hot water 12 smoothly throughout the electrode pad 17.

The electric therapeutic device according to the present invention has the configurations as described above so that it is applied to the treatment of the affected part of a user on the basis of the action of electric current that is generated from the electrode surface 23 of the electrode 16 and flows through the affected part thereof in such a state that the aperture 18 of the conductor 3 is in contact with the affected part thereof.

Upon the treatment of the affected part of the user, the operation of the water circulator 4 is operated to circulate hot water or cold water 12 through the inside of the conductor 3. The operation of the suction pump 7 of the water circulator 4 allows the hot water or cold water 12 in the water reservoir 6 to enter into the conductor 3 through the supply pipe 8. The water 12 then flows through the supply passage 24 of the electrode 16, the circulating passage 30 of the electrode pad 17 and the return passage 26 of the electrode 16 to the conductor 3, and it is discharged through the return pipe 9 therefrom and returns to the water reservoir 6. In this case, the suction pump 7 is configured so as to adjust its suction pressure at an appropriate level in accordance with the height of a site on which the conductor 3 is attached. Further, the water temperature of the hot water or cold water 12 can be adjusted by the action of a heater 11.

The circulation of the water by the water circulator 4 can maintain the electrode pad 17 in a wet state so that the water is always present between the affected part of a user and the electrode surface 23 of the electrode 16. The long-lasting presence of water in the electrode pad 17 can serve as improving the effects of the action of water, eventually the therapeutic effects, expected to be achieved by the electric therapeutic device 1.

Further, the circulation of the water 12 maintained at an appropriate temperature can also maintain the affected part of a user at an optimal level, thereby giving, comfort feeling to the user and improving the therapeutic effects by the electric therapeutic device 1.

Moreover, the air present in the case 13 of the conductor 3 can be sucked out therefrom by the suction pump 7 so that the force of attachment of the conductor 3 to the affected part of the user can be rendered high and the ability of attaching the conductor 3 to the affected part thereof can be improved, too.

INDUSTRIAL UTILIZABILITY OF THE INVENTION

The present invention can be practiced in the manner as described above so that the electric therapeutic device according to the present invention can give the merits as will be described hereinafter.

(1) As the electric therapeutic device of this invention is provided with the water circulator adapted so as to circulate hot water or cold water through the conductor, the conductor can be maintained in a wet state by circulating the water in the conductor by means of the water circulator so that the water can be always present between the affected part of a user and the electrode of the conductor attached thereto. This configuration of the electric therapeutic device can improve the effects to be achieved on the basis of the action of the water by operating the water circulator.

Further, the circulating water is maintained at an appropriate temperature so that the affected part of the user can also be stayed at an optimal temperature level. This can also serve as improving comfort upon using the electric therapeutic device and the operability of the device. In addition, the electric therapeutic device can improve the effects by the action of water so that the high achievements can be gained.

(2) As the water reservoir is communicated with the conductor through the suction pump, the water circulator can circulate water in the conductor by the suction pump so that the comfort feelings as well as the therapeutic effects can be improved.

Moreover, the air within the conductor can also be sucked out so that the conductor can be attached readily and firmly on the affected part of a user simply by placing the conductor thereonto. This can serve as improving the attachment of the conductor to the affected part thereof so that the therapeutic effects can also be achieved by the electric therapeutic device of this invention.

(3) The electric therapeutic device of this invention has the conductor provided with an opening on the bottom of the case and the electrode disposed at the upper portion of the case. Further, the electrode is communicated with the water circulator. This configuration of the electric therapeutic device can circulate water smoothly in the case so that the comfort feeling and the therapeutic effects can be improved.

(4) The conductor has the opening formed on the bottom of the case and the electrode disposed at the upper portion of the case and the electrode pad having water absorbability is disposed right under the electrode. Moreover, the electrode pad or the case is provided with a circulating passage for circulating hot water or cold water so that the water can be circulated through the electrode pad. The circulation of the water in the electrode pad can serve as improving the comfort feeling and the therapeutic effects to be achieved by the electric therapeutic device according to the present invention.

What is claimed is:

1. An electric therapeutic device for treating an affected part of a user by the action of electricity flowing from a conductor attached to the affected part thereof; comprising:

a case;

a conductor;

a water circulator attached to said conductor for circulating hot water or cold water in said conductor, said water circulator comprising a suction pump for circulating water and sucking air present in said conductor;

wherein said conductor has an opening formed on the bottom of said case and an electrode disposed at the upper portion of said case; and an electrode pad is disposed under said electrode; and wherein said electrode pad and case is provided with a circulating passage for circulating hot water or cold water; and wherein said circulating passage comprises a central communicating passage, a bottom communicating passage, and a side communicating passage, said central communicating passage being disposed in a central portion of said electrode pad, said bottom communicating passage communicating with the central communicating passage at its one end and being disposed at a bottom portion thereof, and said side communicating passage communicating with the other end of the bottom passage at its one end and being disposed at a side portion thereof.

2. The electric therapeutic device as claimed in claim 1, wherein said water circulator has a water reservoir; said water reservoir is connected to said conductor through a water supply pipe; and said conductor is connected to said suction pump through a water return pipe.

3. The electric therapeutic device as claimed in claim 2, further comprising a case, and wherein said conductor has an opening formed on the bottom of said case and an electrode disposed at the upper portion of said case; and said electrode is connected to said water circulator.

4. The electric therapeutic device as claimed in claim 1, wherein said electrode is connected to said water circulator.

5. The electric therapeutic device as claimed in claim 1, wherein the suction pump is configured and arranged such that air present in said conductor can be sucked by the suction pump to allow said conductor to be attached closely to the affected part of the user.

6. The electric therapeutic device as claimed in claim 1, wherein the electrode includes a supply side on a top end thereof and a return side on another end of the electrode, and wherein said central communicating passage communicates with a communicating passage formed on the supply path side in said electrode at a top end thereof and said side communicating passage communicates with a communicating passage on the return path side of said electrode at the other end thereof.

7. The electric therapeutic device as claimed in claim 1, wherein the electrode includes a supply side on a top end thereof and a return side on another end of the electrode, and wherein said bottom communicating passage is formed of a plurality of passages and said side communicating passage is formed corresponding to the plurality of said bottom communicating passages, each bottom communicating passage communicating with said central communicating passage.

8. The electric therapeutic device as claimed in claim 1, wherein said electrode pad has water absorbability.

9. The electric therapeutic device as claimed in claim 1, further comprising a temperature control for adjusting the temperature of the circulating water.

10. An electric therapeutic device for treating an affected part of a user, comprising:
    an oscillator for generating electromagnetic waves for use in treating the affected part thereof;
    a conductor connected to said oscillator; and
    a water circulator for circulating hot or cold water to said conductor;
    wherein said conductor has an electrode accommodation section at an upper portion thereof and an electrode pad accommodation section at a lower portion thereof, said electrode accommodation section having an electrode disposed therein and said electrode pad accommodation section having an electrode pad disposed therein;
    wherein said electrode is provided with a first communicating passage on a supply path side and a second communicating passage on a return path side; and
    wherein said electrode pad is provided with a third communicating passage communicating with an exit end of said first communicating passage of said electrode at an inlet side end thereof and communicating with an inlet end of said second communicating passage of said electrode at an exit side end thereof.

11. The electric therapeutic device as claimed in claim 10, wherein:
    said conductor is connected to said oscillator through a first connection means; and
    said first connection means is coupled with a second connection means.

12. The electric therapeutic device as claimed in claim 11, wherein said first connection means is composed of a metal wire.

13. The electric therapeutic device as claimed in claim 11, wherein said second connection means comprises at least one of said first, second, and third communicating passages and is composed of a pipe.

14. The electric therapeutic device as claimed in claim 11, further comprising a case connected to said conductor through said second connection means; said case containing said oscillator, a water reservoir and a suction pump; wherein:
    said oscillator is connected to said conductor through said first and second connection means, said first connection means being connected to the second connection means;
    said second connection means comprises a communicating supply passage on a supply path side and a communication return passage on a return path side;
    said communicating return passage is provided with said suction pump; and
    said suction pump can suck air present in the conductor.

15. The electric therapeutic device as claimed in claim 10, wherein said third communicating passage of said electrode pad comprises a central communicating passage, a bottom communicating passage, and a side communicating passage, said central communicating passage being disposed in a central portion of said electrode pad, said bottom communicating passage communicating with the central communicating passage at its one end and being disposed at a bottom portion thereof, and said side communicating passage communicating with the other end of the bottom passage at its one end and being disposed at a side portion thereof.

16. The electric therapeutic device as claimed in claim 15, wherein an inlet end of said central communicating passage communicates with the exit end of said first communicating passage of said electrode and an exit end of said side communicating passage communicates with an inlet end of said second communicating passage of said electrode.

17. The electric therapeutic device as claimed in claim 15, wherein said bottom communicating passage is formed of a plurality of passages and said side communicating passage is formed corresponding to said plurality of said bottom communicating passages, each bottom communicating passage communicating with said central communicating passage.

18. The electric therapeutic device as claimed in claim 10, further comprising a case connected to said conductor through said second connection means; said case containing said oscillator, a water reservoir and a suction pump; wherein:
    said oscillator is connected to said conductor through said first and second connection means, said first connection means being connected to the second connection means;
    said second connection means comprises a communicating supply passage on a supply path side and a communication return passage on a return path side;
    said communicating return passage is provided with said suction pump; and
    said suction pump can suck air present in the conductor.

* * * * *